(12) United States Patent  (10) Patent No.: US 8,123,354 B2
Olivier et al.  (45) Date of Patent: Feb. 28, 2012

(54) COMPACT ADAPTIVE OPTIC-OPTICAL COHERENCE TOMOGRAPHY SYSTEM

(75) Inventors: Scot S. Olivier, Livermore, CA (US); Diana C. Chen, Fremont, CA (US); Steven M. Jones, Danville, CA (US); Sean M. McNary, Stockton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 13/085,123

(22) Filed: Apr. 12, 2011

(65) Prior Publication Data

US 2011/0194072 A1  Aug. 11, 2011

Related U.S. Application Data

(60) Division of application No. 12/690,855, filed on Jan. 20, 2010, now Pat. No. 7,942,527, and a continuation-in-part of application No. 11/874,832, filed on Oct. 18, 2007, now Pat. No. 7,665,844.

(60) Provisional application No. 61/146,575, filed on Jan. 22, 2009, provisional application No. 60/852,857, filed on Oct. 18, 2006.

(51) Int. Cl.
A61B 3/14 (2006.01)
A61B 3/10 (2006.01)
A61B 3/00 (2006.01)

(52) U.S. Cl. .................... 351/206; 351/221; 351/246

(58) Field of Classification Search ........... 351/200–246
See application file for complete search history.

(56) References Cited

U.S. PATENT DOCUMENTS 4,660,945 A  4/1987  Trachtman
(Continued)

Primary Examiner — Mohammed Hasan

(57) ABSTRACT

Badal Optometer and rotating cylinders are inserted in the AO-OCT to correct large spectacle aberrations such as myopia, hyperopic and astigmatism for ease of clinical use and reduction. Spherical mirrors in the sets of the telescope are rotated orthogonally to reduce aberrations and beam displacement caused by the scanners. This produces greatly reduced AO registration errors and improved AO performance to enable high order aberration correction in a patient eyes.

4 Claims, 10 Drawing Sheets

U.S. PATENT DOCUMENTS

| | | |
|---|---|---|
| 5,002,384 A | 3/1991 | Trachtman |
| 5,208,619 A | 5/1993 | Campbell |
| 6,199,986 B1 * | 3/2001 | Williams et al. .............. 351/221 |
| 6,338,559 B1 | 1/2002 | Williams et al. |
| 6,890,076 B2 * | 5/2005 | Roorda .......................... 351/205 |
| 2001/0016695 A1 * | 8/2001 | Mihashi et al. ............... 600/558 |
| 2008/0284979 A1 | 11/2008 | Yee et al. |

* cited by examiner

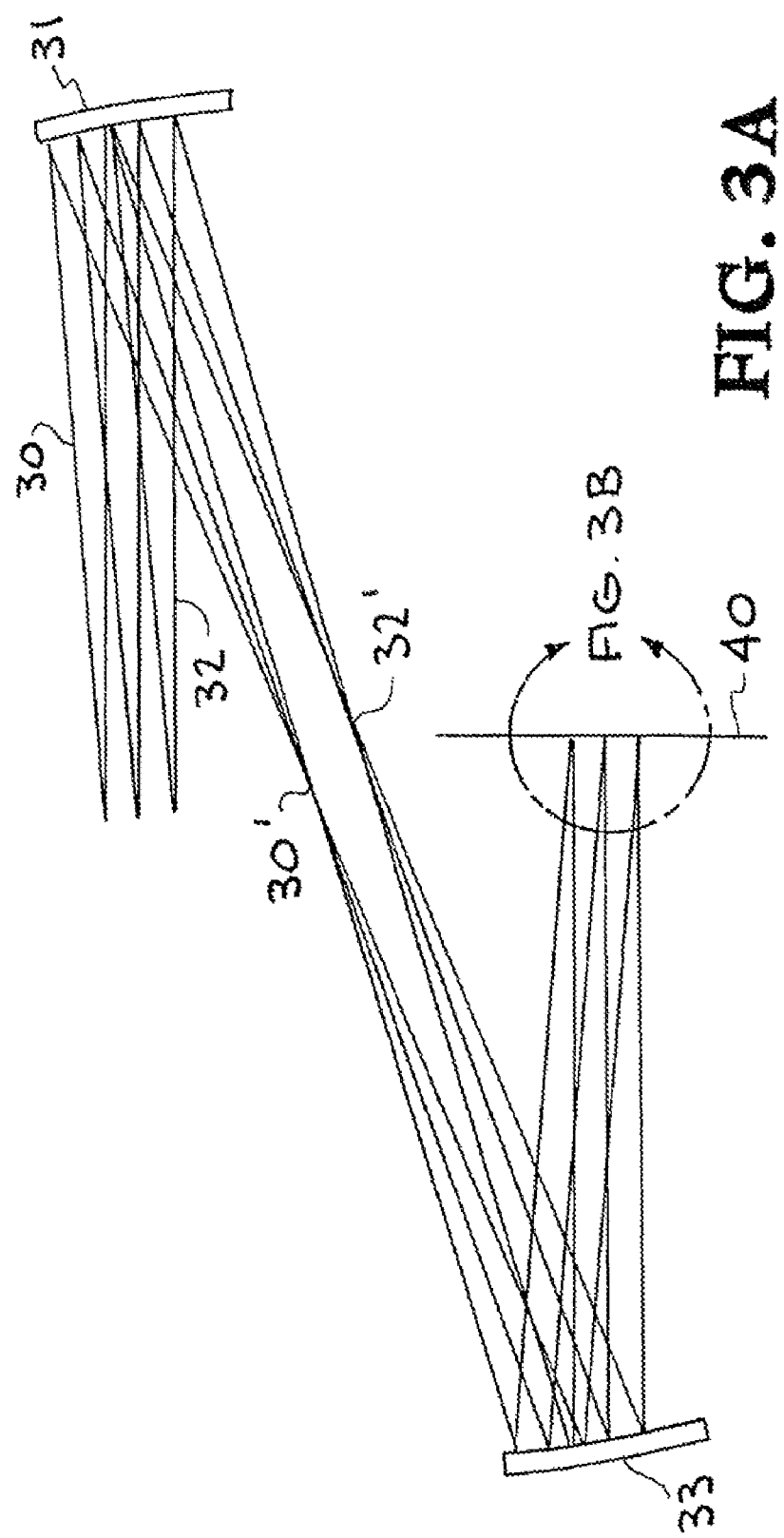

COMPACT ADAPTIVE OPTIC-OPTICAL COHERENCE TOMOGRAPHY SYSTEM

This application is a divisional of U.S. patent application Ser. No. 12/690,855, filed Jan. 20, 2010 now U.S. Pat. No. 7,942,527 B2, titled, "Compact Adaptive Optic-Optical Coherence Tomography System," incorporated herein by reference. U.S. patent application Ser. No. 12/690,855 now U.S. Pat. No. 7,942,527 B2 claims priority to U.S. Provisional Patent Application Ser. No. 61/146,575, filed Jan. 22, 2009, titled, "Compact Adaptive Optic-Optical Coherence Tomography System," incorporated herein by reference. U.S. patent application Ser. No. 12/690,855 now U.S. Pat. No. 7,942,527 B2 is a continuation-in-part of U.S. patent application Ser. No. 11/874,832 now U.S. Pat. No. 7,665,844 B2 titled, "High-resolution Adaptive Optics Scanning Laser Ophthalmoscope with Multiple Deformable Mirrors," filed Oct. 18, 2007, incorporated herein by reference. U.S. patent application Ser. No. 11/874,832 claims priority to U.S. Provisional Patent Application Ser. No. 60/852,857, filed Oct. 18, 2006, titled, "High Resolution Adaptive Optics. Scanning Laser Ophthalmoscope with Multiple Deformable Mirrors," incorporated herein by reference.

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

1. Field of the Invention

The present invention relates to optical coherence tomography, and more specifically, it relates to the use of adaptive optics in optical coherence tomography for retinal imaging.

2. Description of Related Art

Optical coherence tomography (OCT) is a leading modality for non-invasive, in vivo imaging of the human retina, providing high sensitivity, speed and axial resolution in quantifying retinal pathology. The lateral resolution of the OCT image of the retina, however, is poor due to ocular aberrations.

Adaptive optics (AO) have been incorporated into OCT systems to increase the lateral resolution by measuring and subsequently compensating for the aberrations in real time. This technology was originally used for correcting image degradation due to atmospheric aberration in astronomy. In recent years, AO technology has been applied to several instruments for retinal imaging, such as flood illumination fundus imaging, scanning laser ophthalmoscopy, and most recently, ophthalmic optical coherent tomography. In an AO system, the ocular aberrations of the test subjects are measured by a wavefront sensor. The measured wavefront errors are then used to adjust the shape of a deformable mirror (DM) until the wavefront aberrations are minimized.

Population studies have shown that many people have both low-order aberrations with large magnitudes and high-order aberrations with small magnitudes. For these subjects, current technology cannot deliver the phase compensation needed using a single deformable mirror (DM). The use of two deformable mirrors has been investigated. An AO-OCT system incorporating two deformable mirrors was demonstrated by Zawadzki et al. The bimorph DM from AOptix used in that OCT system had a relatively high dynamic range and could correct defocus and astigmatism up to ±3D. This obviated the need for the meticulous use of trial lenses to correct the refractive errors of a subject. The system included a micro-electro-mechanical system (MEMS) DM (from Boston Micro Machine) that had 144 pixels and 1.5 μm stroke, which was used to correct the residual high-order aberrations left by the bimorph DM compensation. Both deformable mirrors were placed in the non-scanning path. Such arrangement, however, generated noticeable beam distortions at the deformable mirrors and the wavefront sensor when large refractive corrections were needed.

In an AO-OCT system demonstrated by Zhang et al., the bimorph mirror was placed one relay telescope away from the eye. This minimized the propagation of ocular refractive errors through the system prior to compensation. This arrangement greatly reduced the pupil distortion at the deformable mirrors and wavefront sensor. However, because the bimorph mirror was placed in the scanning path (i.e., between the eye and scanners), the beam at the eye pupil shifted with the changing incidence angles of the light as the beam was steered by the scanners. This would result in degradation of the AO-OCT system.

SUMMARY OF THE INVENTION

It is an object of the present invention to provide a compact AO-OCT system that includes a Badal optometer and rotating cylindrical lenses to compensate for defocus and astigmatism, respectively, and a micro-electro-mechanical system (MEMS)-based adaptive optic to compensate for high-order aberrations.

This and other objects will be apparent based on the disclosure herein.

Embodiments of the present invention include an optical apparatus to correct the spectacle aberrations of patients. Such aberrations include myopia, hyperopia and astigmatism. Residual aberrations are compensated by a MEMS DM, which is placed between the light source, e.g., a superluminescent diode (SLD) light source, and the XY scanners in the AO-OCT system, to minimize the pupil shift at the MEMS. In addition, the compact AO-OCT system is optimized to have minimum system aberrations to reduce AO registration errors and improve AO performance. Unlike the previous large systems which were set-up on a standard lab table, embodiments of the present AO-OCT system are specifically designed for clinical use requiring compact size, low cost, and high reliability.

Accordingly, embodiments of compact MEMS-based adaptive optic (AO) optical coherence tomography (OCT) systems with improved AO performance and ease of clinical use are described. Adaptive optic systems often consist of a Shack-Hartmann wavefront sensor and a deformable mirror that measures and corrects ocular and system aberrations. Because of limitations on current deformable mirror technologies, the amount of real-time ocular-aberration compensation is restricted and small in previous AO-OCT instruments. The present invention eliminates the tedious process of using trial lenses in clinical imaging. Different amounts of spectacle aberration compensation are achieved, e.g., by motorized stages, and automated with the AO computer for ease of clinical use. In addition, embodiments of the present invention include a compact AO-OCT system that is optimized to have minimum system aberrations to reduce AO registration errors and improve AO performance.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 3A is an illustration of beam shift for different field angles in an afocal telescope.

DETAILED DESCRIPTION OF THE INVENTION

Figure 1:
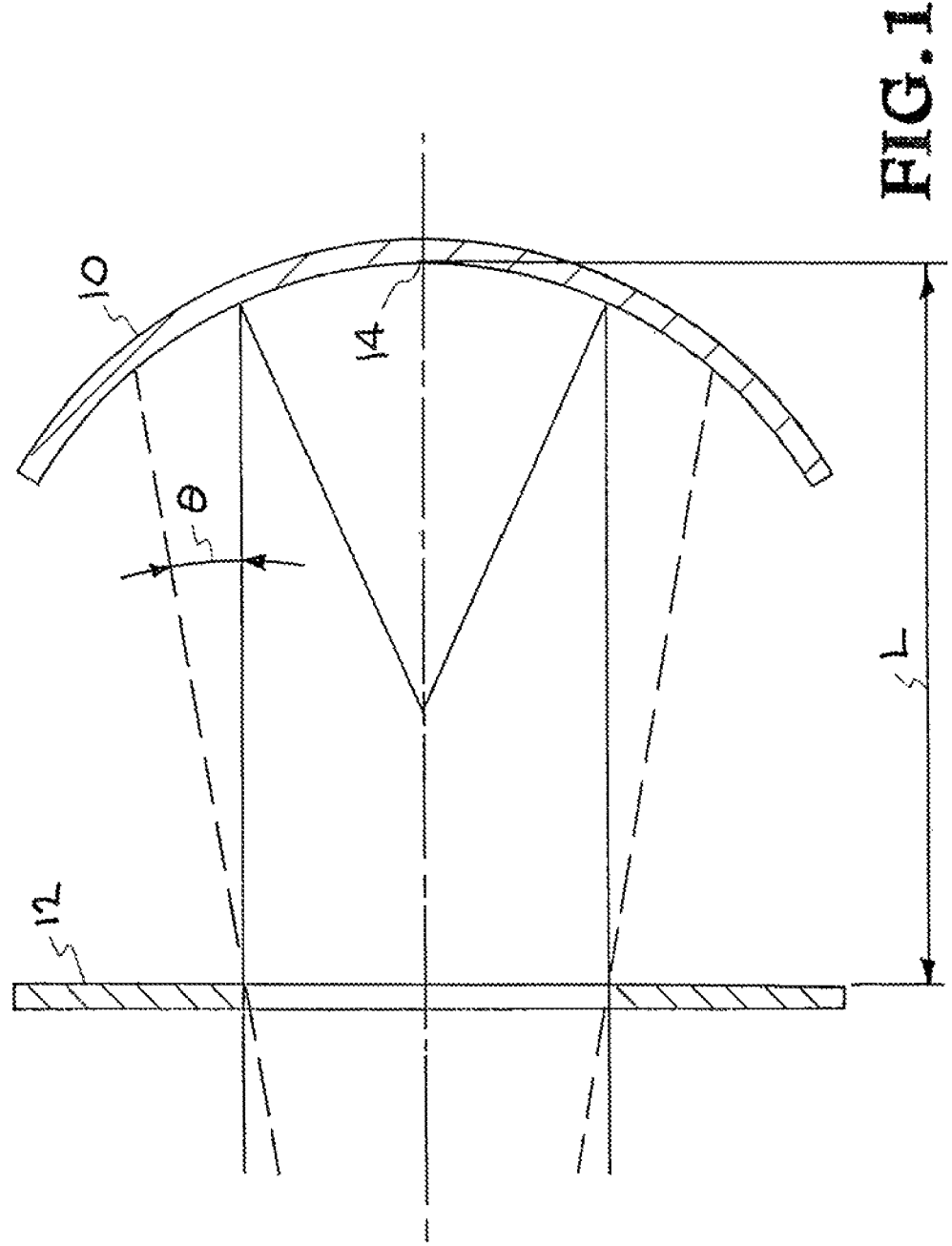
FIG. 1 is an illustration of a spherical mirror.

Embodiments of the present invention include an AO-OCT system consisting of three channels: (1) a sample (or signal) channel, equipped with an AO for collecting the retinal image, (2) a reference channel with an optical path length matching that of the sample channel, and (3) detection channel for recording the combined sample and reference signals. The sample channel length is from the beamsplitter (BS) (e.g., from an 80/20 BS) to the target and back to the splitting point of the BS. The reference channel length is from the BS to a mirror at the end of the channel and back.

TABLE 1

Summary of exemplary system components

| | |
|---|---|
| Light source | Superluminescent diode (SLD) from Superlum $\lambda$ = 842 nm, $\delta\lambda$ = 50 nm |
| Deformable mirror | MEMS from Boston Michomachines Corp. 3.3 mm × 3.3 mm optical aperture, 12 × 12 actuators 1.5 µm stroke |
| Horizontal/vertical scanners | Cambridge Technology; 6220M40 galvanometric scanner, ±20° |
| Wavefront sensor | Shack-Hartmann wavefront sensor Lens array from Adaptive Optics Associates 20 × 20 elements, 500 µm pitch, 30 mm focal length and CCD camera from Dalsa |
| Diffraction grating | Holographic transmitting diffraction grating from Wasatch Photonics 1200 lines/mm |
| CCD camera | Line-scan camera from Atmel, 12 bit, 2048 pixels |

In an embodiment, in the sample channel, the light from a broadband superluminescent diode (SLD) is coupled into a single mode fiber. The light is then collimated and relayed by mirror telescopes to a deformable mirror, the horizontal and vertical scanners, the spherical-cylindrical correction apparatus and finally to the eye. Each component is placed at the image plane of an afocal relay telescope. Spherical mirrors, instead of lenses, are used in the afocal telescope design to reduce back-reflections and minimize chromatic aberrations in the system. This is important because the spectrum of the light source must be very broad to achieve high axial resolution. The off-axis configuration of the reflective spherical mirrors, however, creates substantial system aberrations. It also results in beam displacement at the pupil of the eye due to scanning in both X-Y directions. Both aberrations and beam displacements result in performance degradation of the AO-OCT system. However, the sample channel in the present invention includes a means to compensate aberrations in realtime to achieve substantial higher lateral resolution.

In the reference channel, the optical path length is matched to that of the sample channel by folding the optical path with several spherical mirrors. In the detection channel, the light from the sample and reference arms is combined by the fiber coupler and sent to a spectrometer-based detector, which in some embodiments is a holographic transmitting diffraction grating focused onto a line-scan charge coupled device (CCD).

As mentioned above, the off-axis configuration of the reflective spherical mirrors creates substantial system aberrations. The deformable mirror is able to compensate a portion of both the optical system aberrations and the ocular aberrations of patients. However, if part of the stroke of the deformable mirror is used to compensate the system aberrations, the magnitude of the compensation of the ocular aberrations is reduced. Furthermore, the aberrations will introduce pupil aberration and distortion, which cause performance degradation of the AO compensation. The present invention minimizes the aberrations from the optical system itself.

Important guidelines in the optical design of embodiments of the present invention can be derived from the magnitudes of aberration produced by a spherical mirror. FIG. 1 is an illustration of a spherical mirror 10 having a radius of curvature (R). The entrance pupil 12 is at distance L from the vertex 14 of the mirror. The incidence angle of the beam is $\theta$. For a single reflective spherical mirror such as the one shown in FIG. 1, the magnitude of aberrations is given in the second column of Table 2.

TABLE 2

| Aberration type | Magnitude | When L = R/2 |
|---|---|---|
| Spherical aberration | $\dfrac{1}{128F^3}$ | $\dfrac{1}{128F^3}$ |
| Coma | $\dfrac{(L-R)\theta}{16RF^2}$ | $\dfrac{\theta}{32F^2}$ |
| Astigmatism | $\dfrac{(L-R)^2\theta^2}{2R^2F}$ | $\dfrac{\theta^2}{8F}$ |

The entrance pupil is at distance L from the vertex of the mirror. F stands for the F-number. For a set of afocal telescopes where L is half of R, the magnitude of the aberrations is simplified in the third column. Examination of the magnitude in detail is provided below.

1) Spherical/Coma/Astigmatism ~$1/F^3$ to $1/F^2$ to $1/F$. Aberrations decrease as the F-number increases. Thus, afocal telescopes with longer focal lengths have smaller aberrations.

2) Spherical/Coma/Astigmatism ~1 to $\theta$ to $\theta^2$. Spherical aberration is independent of the tilt angle of the reflective mirror. Both coma and astigmatism increase as the tilt angle increases, so afocal telescopes having a smaller tilt angle will have smaller aberrations.

3) Spherical/Coma/Astigmatism=1 to $4\theta F$ to $(4\theta F)^2$. For a mirror with a radius of curvature of 0.5 m, an entrance pupil diameter of 10 mm and a tilt angle of 5°, the ratio of Spherical/Coma/Astigmatism=1 to 8.7 to 75.7. In most cases, astigmatism is the dominating aberration in the system.

In addition, most telescopes typically form images over a curved surface instead of a flat surface. The aberration of the field curvature can be expressed as a defocus term $\theta^2/16R_pF^2$ where $R_p$ is the radius of Petzval field curvature. A system with small tilt angle and large focal length thus has smaller aberration due to field curvature.

Figure 2A:
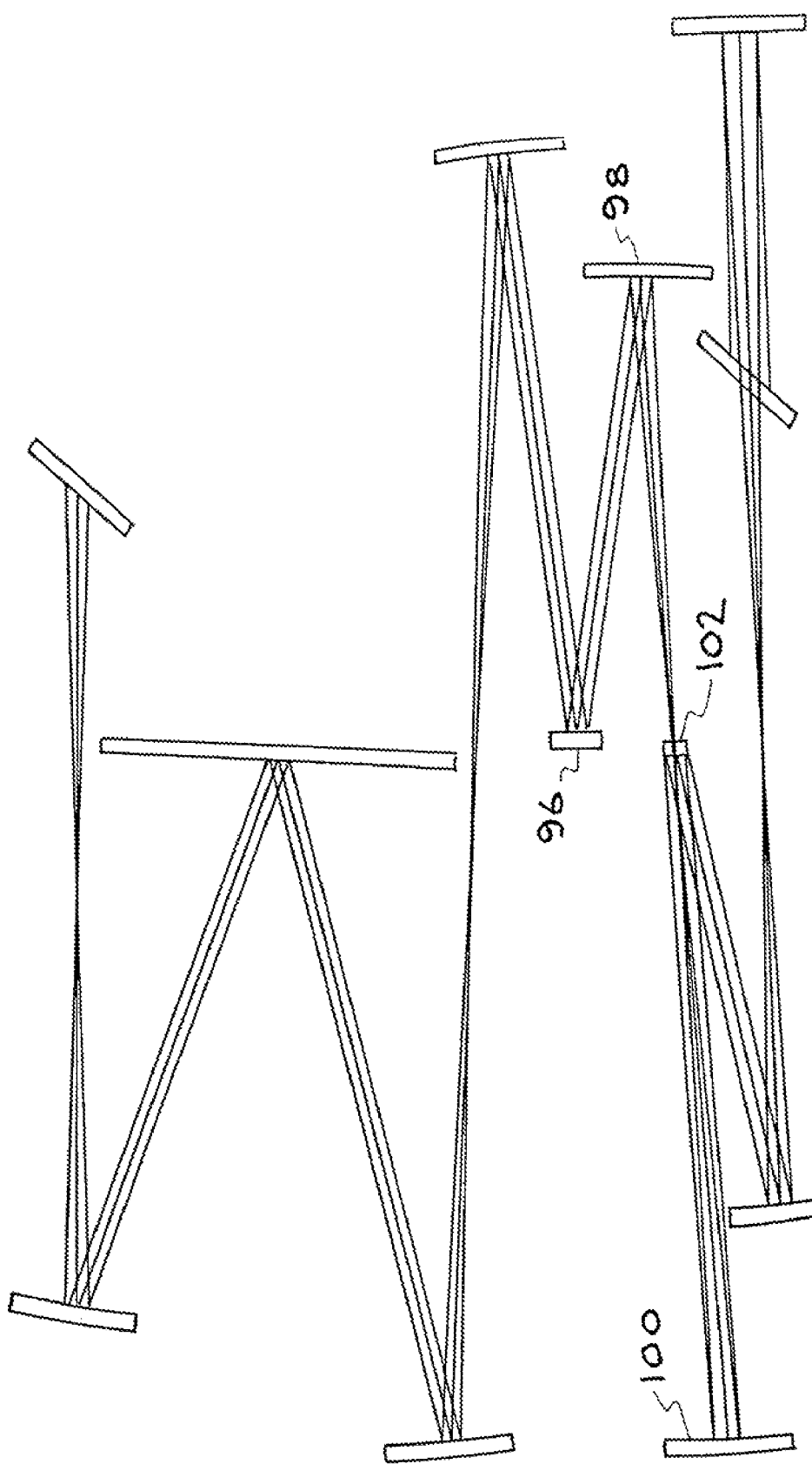
FIG. 2A shows the optical layout in the YZ plane of an AO-OCT sample channel.
Figure 2B:
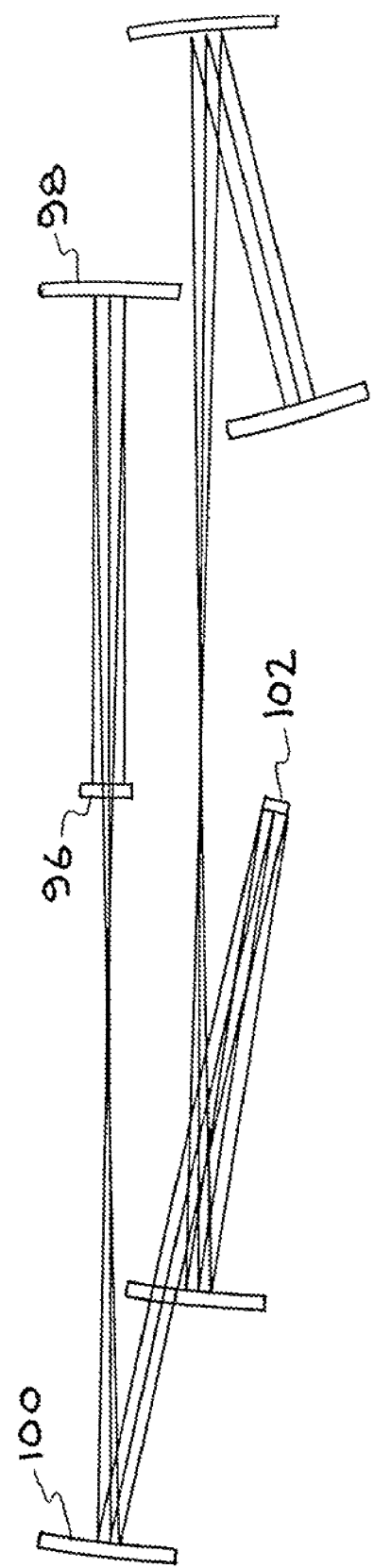
FIG. 2B shows the optical layout in the XZ plane of an AO-OCT sample channel.

FIG. 2A shows the optical layout in the YZ plane of an embodiment of an AO-OCT sample channel. The present invention removes system aberration. The references numbers are identical to those used in FIGS. 7A and 7B because the elements and configuration are identical. Astigmatism is removed in the following configuration. If the optical layout is made on a table top, the view of FIG. 2A would be a top view. FIG. 2B shows the optical layout of FIG. 2A in the XZ plane. Again, if the optical layout is made on a table top, the view of FIG. 2B would be a side view from the bottom edge of FIG. 2A. The two mirrors (98, 100) in the relay telescope between horizontal scanner and vertical scanner are tilted orthogonally. The amount of tilt is determined by the amount of astigmatism produced from the reflections by the spherical mirrors. The amount of tilt therefore is set to remove the astigmatism.

The above description presents some challenges for the design of a compact AO-OCT system. For example, long focal lengths result in a large footprint and small tilt angles cause physical conflicts between components. Embodiments of the present invention minimize the total aberrations by targeting astigmatism because it is the dominating aberration in the afocal telescope. By tilting the second spherical mirror 100 of the afocal telescope in the orthogonal plane, the two spherical mirrors canceled the astigmatism that would be introduced by a single mirror. An additional benefit is derived because the mirrors are placed at different heights, so the physical conflict is less an issue for the smaller tilt angles. The two mirrors (98, 100) in the relay telescope between horizontal scanner and vertical scanner are tilted orthogonally. The Y-scanning mirror 102 is placed in the same line between the two mirrors (98, 100) in the YZ plane, but at a different height. This leads to a compact design and can be used to correct for system aberrations as discussed below.

In one embodiment, light is scanned on the retina in a raster pattern With a horizontal scanner and a vertical scanner (mirrors 96 and 102 in FIGS. 2A and 2B). These mirrors can each be mounted on a galvanometric scanner (e.g., Cambridge Technology; 6220M40 galvanometric scanner, ±20°). The two scanners are separated by a relay telescope (mirrors 98 and 100 in FIGS. 2A and 2B) designed to make them optically conjugate to each other and to the entrance pupil of the eye. This minimizes the movement of the scanning beam at the pupil.

Figure 3B:
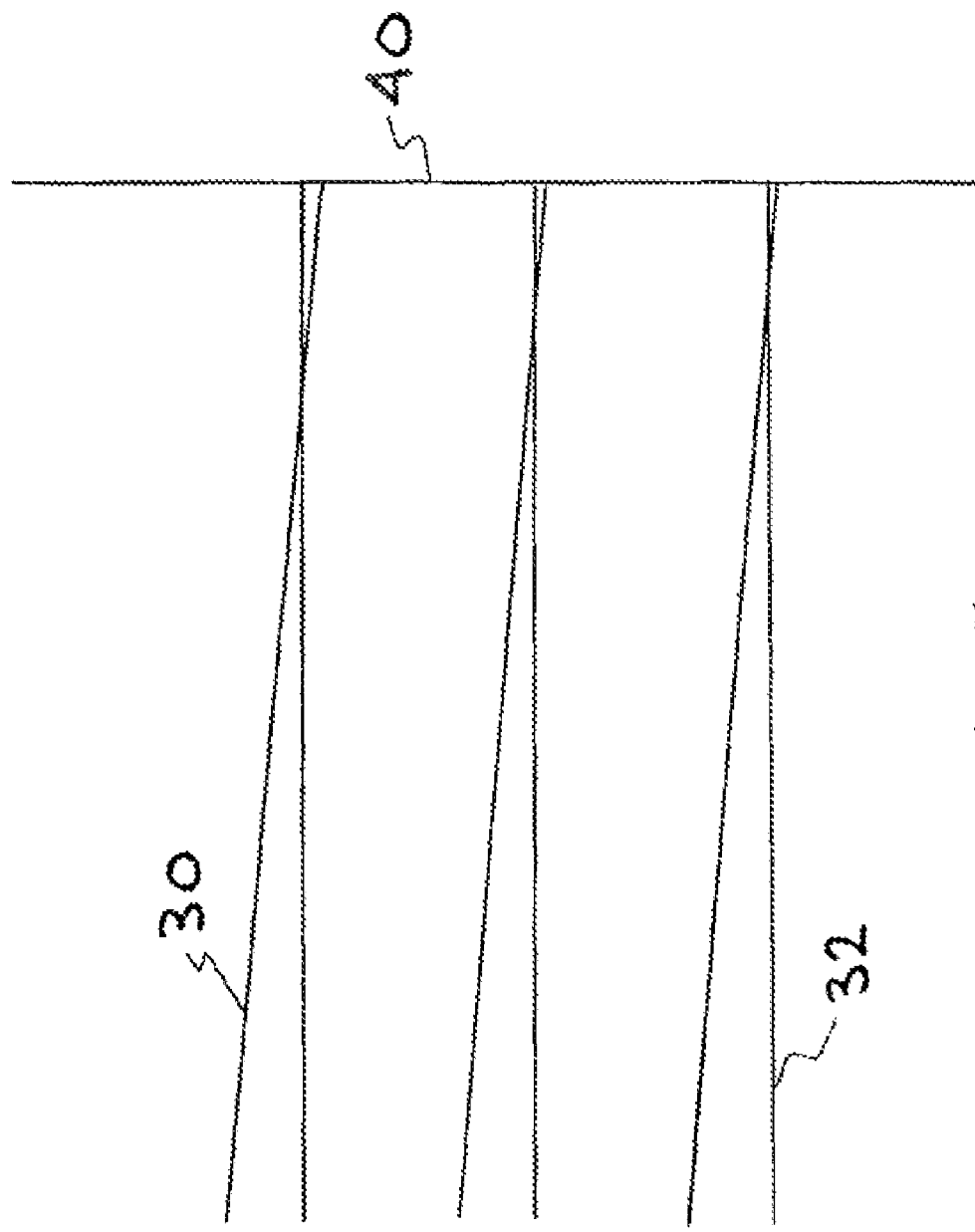
FIG. 3B is a magnified view of the region of FIG. 3A near the image plane.

FIG. 3A is an illustration of a beam shift for different field angles in an afocal telescope. A beam 30 is focused at 30' by spherical mirror 31 and is then reflected by mirror 33 to image plane 40. Another beam 32 is directed at spherical mirror 31 at a different angle than that of beam 30. Beam 32 is focused at 32' and then reflected from spherical mirror 33 to image plane 40. FIG. 3B is a magnified view of the region of FIG. 3A near the image plane 40. Notice the slight difference in position of beams 30 and 32 on image plane 40. In operation, the chief rays from various field angles do not all pass through the center of the pupil and thus, the beam is shifted as a function of the field angle. This will degrade the system performance in several ways. First, this will cause beam clipping at the pupil, which causes intensity fluctuation as a function of scanning angle. Second, the phase correction the DM would apply would depend on the scanning angle, thereby resulting in the AO system suffering a kind of anisoplanatism. Third, the speed of the scanners is much faster than the response time of the wavefront sensor and the DM. Hence, the Shack-Hartmann wavefront sensor would measure the averaged wavefront and high spatial frequency aberrations would be averaged out and uncompensated. Both horizontal and vertical scanners produce beam shifts. The shifts have to be minimized for the optimal performance. It is desirable that the shift is less than half of the sub-aperture at the Shack-Hartman wavefront sensor.

Figure 4B:
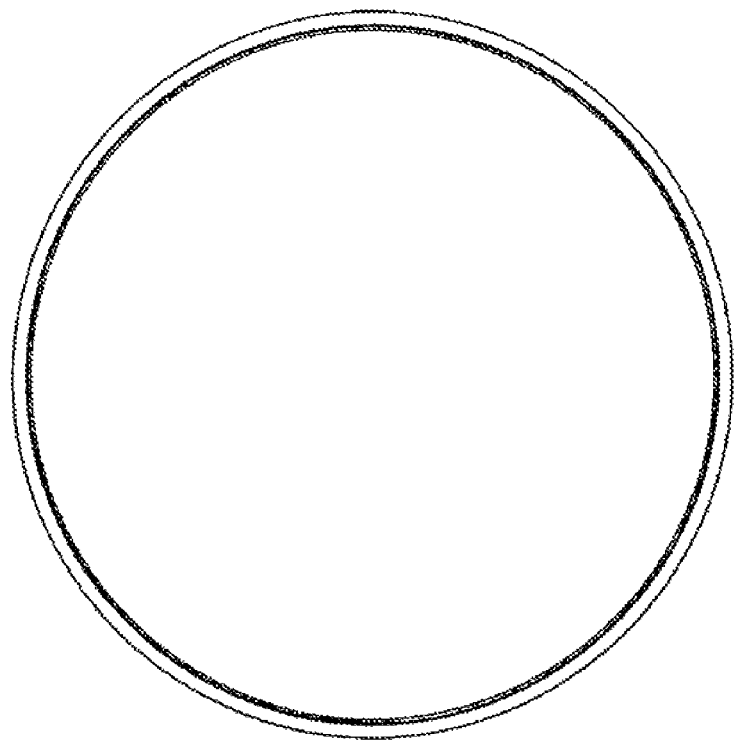
FIG. 4B shows small beam shift when mirrors are rotated orthogonally at various scanning angles at the pupil plane of the eye of the AO-OCT design.
Figure 4A:
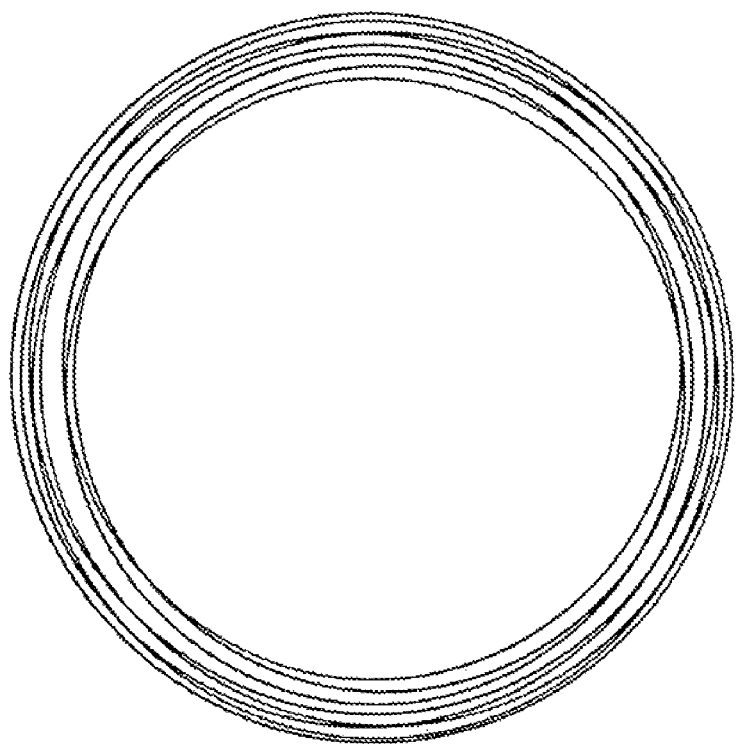
FIG. 4A shows large beam shifts when mirrors are rotated in the same planes of various scanning angles at the pupil plane of the eye of the AO-OCT design.

FIGS. 4A and 4B illustrate the beam shifts of various scanning angles at the pupil plane of the eye of the AO-OCT design. FIG. 4A shows large beam shifts when mirrors are rotated in the same planes of various scanning angles at the pupil plane of the eye of the AO-OCT design. FIG. 4B shows small beam shifts when mirrors are rotated orthogonally at various scanning angles at the pupil plane of the eye of the AO-OCT design. The beam shift is proportional to the tilt angle of the reflective mirror and the F-number. So a smaller radius of curvature of the reflective mirror is preferred to minimize the beam displacement due to the scanning. This is beneficial for a compact design. However, a small radius of curvature of the mirrors would increase aberrations. Radii of curvatures were compromised to meet the design specification of both aberrations and beam displacements. By rotating the second mirror orthogonally to the first mirror in the afocal telescope, both aberrations and beam displacements are reduced.

In an exemplary layout of an optical apparatus designed for spectacle aberration compensation, defocus is compensated by a Badal optometer and astigmatism is compensated by rotating cylinders. Badal lenses and rotating cylinders are used to compensate the large spectacle aberrations in the design of the AO-OCT for clinical use because of the limitations of the deformable mirrors. Current deformable mirror technology has limited stroke, and many of them have not been yet proven sufficiently reliable for long-term clinical testing.

Figure 5:
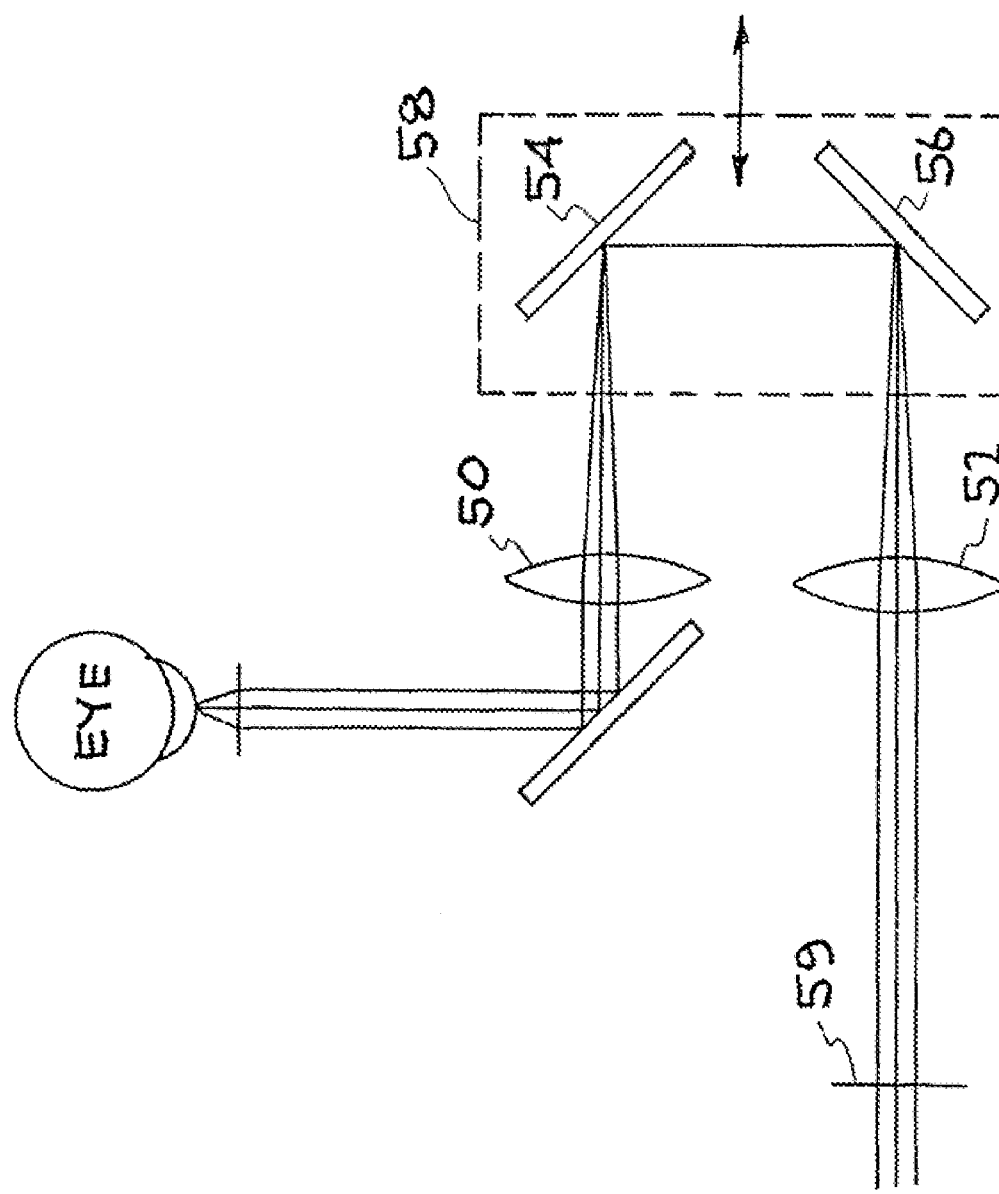
FIG. 5 shows the layout of an optical apparatus for spectacle aberration compensation.
Figure 6:
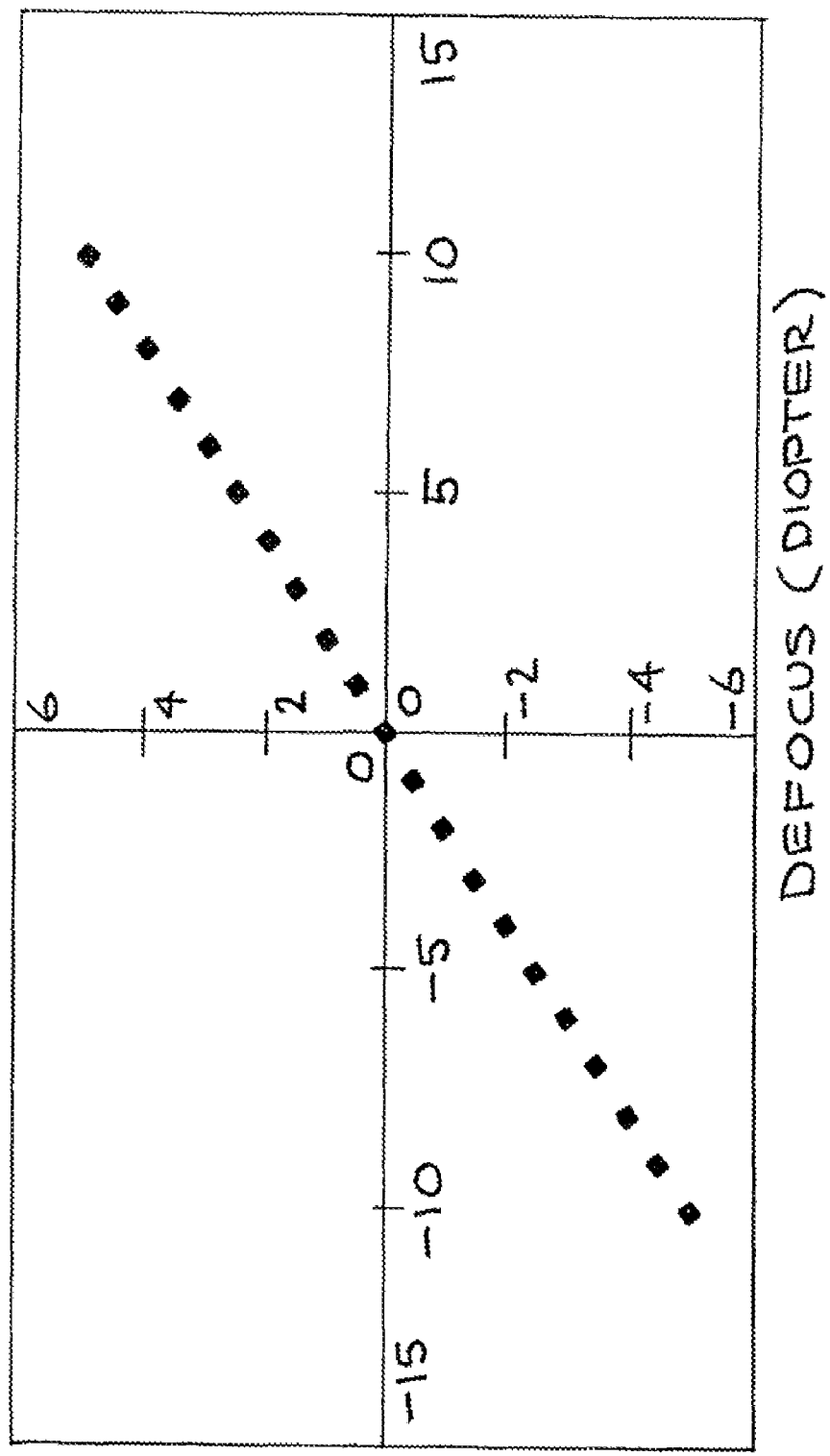
FIG. 6 shows amount of defocus compensated versus the moving distance of the stage of the Badal optometer.

In an embodiment shown in FIG. 5, the Badal optometer includes two achromatic transmissive lenses (50, 52) with focal lengths of 100 mm, and further includes two folding reflective mirrors (54, 56). The two folding mirrors are located on and controlled by one motorized translation stage 58. The two rotating cylinders 59 are placed at the conjugate plane of the eye pupil to compensate for the astigmatism in the eye. FIG. 6 shows the amount of defocus compensated versus the moving distance of the stage. The amount of defocus the apparatus could compensate was linear to the moving distance of the two mirrors.

Figure 7A:
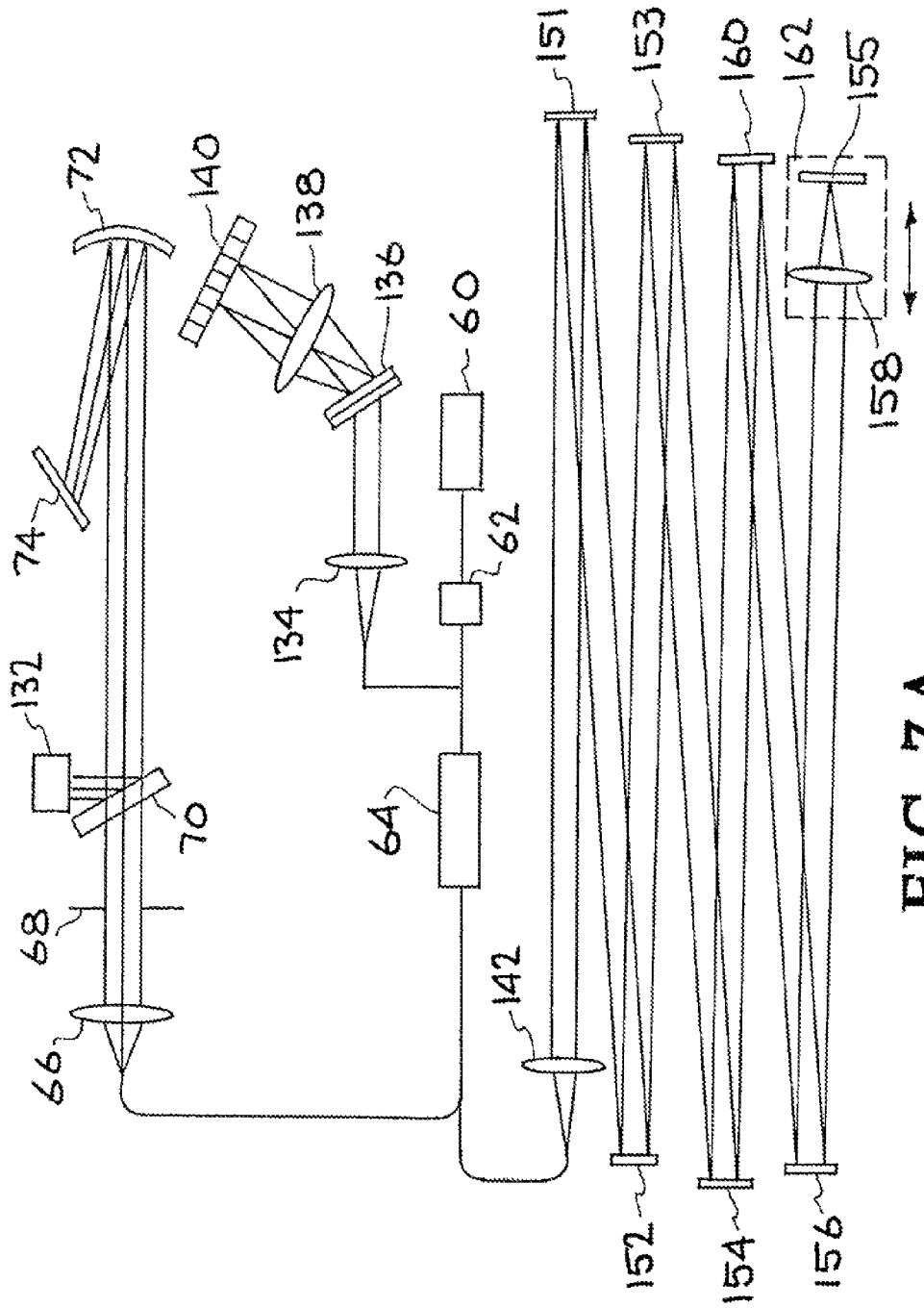
FIG. 7A shows an embodiment of a present AO-OCT optical system layout for a reference channel and detection channel.
Figure 7B:
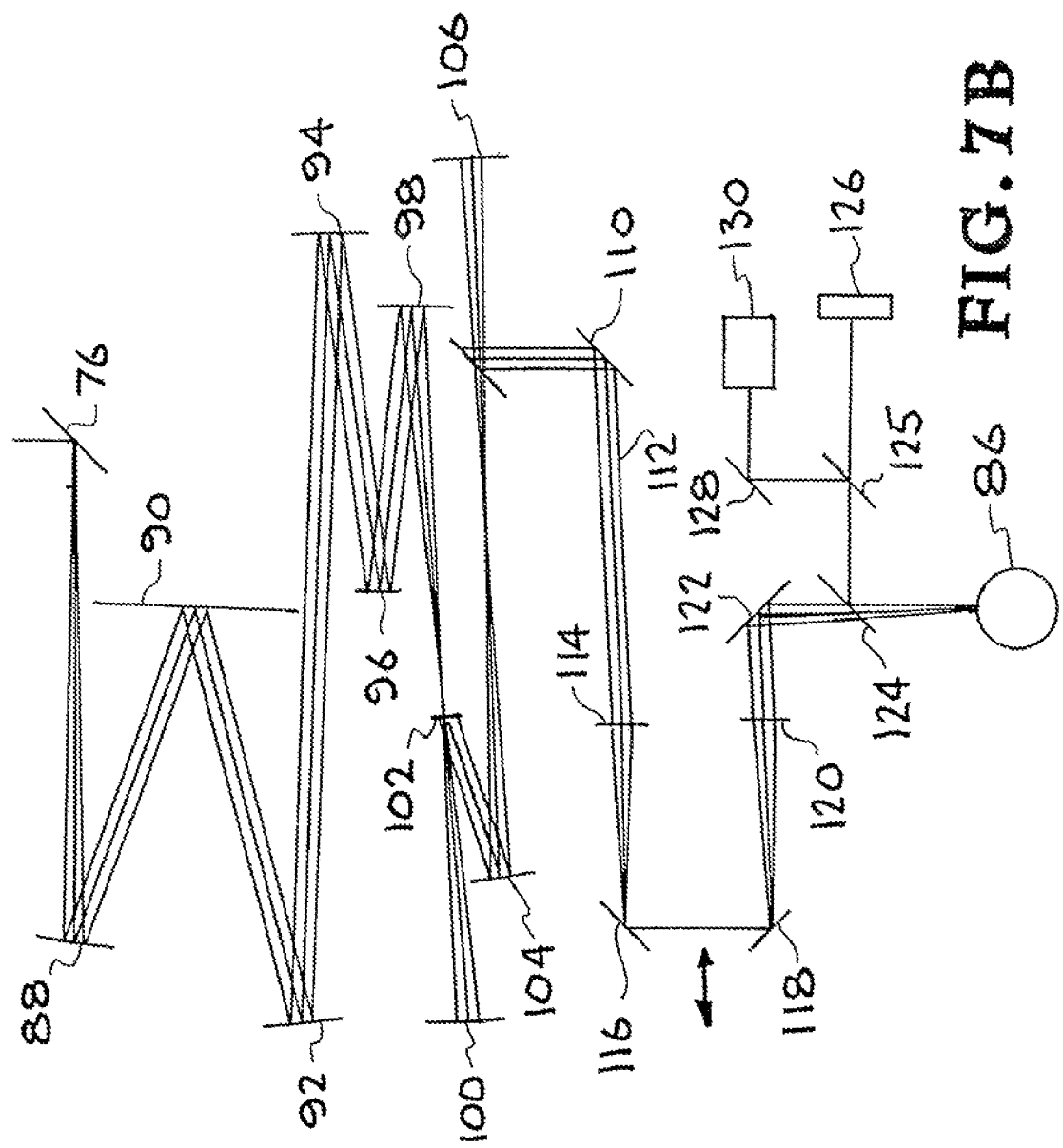
FIG. 7B shows an embodiment of a present AO-OCT optical system layout for a sample channel.

FIG. 7A shows an optical system layout for a reference channel and detection channel for an embodiment of the present AO-OCT system. FIG. 7B shows a sample channel for an embodiment of the present AO-OCT system. To make the AO-OCT system compact, the sample channel is set-up on one optical breadboard and the detection channel/reference channel is set up on a second optical breadboard. The two breadboards are stacked together by supporting posts.

Referring to FIG. 7A, superluminescent laser diode 60 produces laser light that passes through an optical isolator 62 and is coupled into 80/20 fiber beamsplitter. (BS) 64. One arm of BS 64 begins the path of the sample channel, and produces a diverging output beam that is collimated by lens 66, the output of which is passes through aperture 68, and beamsplitter 70 to be reflected from spherical mirror 72. (Another arm of BS 64 is passed through a reference channel as discussed below.) The beam is then directed to a first telescope mirror 74 (which can be a spherical mirror) that directs the beam upwards to a second telescope mirror 76 (which can be a spherical mirror), which is shown on FIG. 7B. Notice that the beam reflected from spherical mirror 72 goes through a number of foci as it traverses the sample channel to the target 86. Thus, from telescope mirror 76 to the target 86 the beam traverses a path consecutively through optics as follows: spherical mirror 88, MEMS adaptive optic 90, spherical mirror 92, spherical mirror 94, scanning mirror 96 (flat), spherical mirror 98, spherical mirror 100, scanning mirror 102 (flat), spherical mirror 104, spherical mirror 106, spherical mirror 108, reflective optic 110, cylindrical lenses 112, achromatic transmissive lens 114, mirror 116, mirror 118, achromatic transmissive lens 120, mirror 122 and beamsplitter 124. The target 86 is intended to be a human eye the gaze of which looks through beamsplitter 125 and is fixed on point 126. The pupil image is directed from beamsplitter 125 to mirror 128 and finally to pupil camera 130.

Light reflected from target 86 travels in reverse back to spherical mirror 72 (FIG. 7A) which reflects the light to beamsplitter 70 and then to SHWS 132. Light traversing beamsplitter 70 is focused back into BS 64, the output of which is collimated with lens 134, dispersed with grating 136, and imaged with lens 138 onto CCD camera 140. Optical isolator 62 prevents the light returning from target 86 from entering the light source 60.

As mentioned above, a second arm of BS 64 (FIG. 7A) is sent to a reference channel where it is collimated with lens 142 and is reflected by mirrors 151-156 to be focused by lens 158 onto mirror 160. Lens 158 and mirror 160 are mounted on a movable stage 162 that is used to change the path length of the reference channel. Light reflected from mirror 160 travels back through BS 64 and onto CCD camera 140 to produce an interference pattern upon interaction with light from target 86.

Alternate components may be substituted for the components described in the embodiment of FIGS. 7A and 7B. Such alternates will be apparent to those skilled in the art based on this description. For example, the light source may be any appropriate light source having a large optical bandwidth and a short coherence length. The system can be configured without the use of a fiber optic beamsplitter, using, e.g., standard beamsplitters, lenses and mirrors.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. An apparatus, comprising
a light source for providing an input beam;
means for splitting said input beam into a reference beam and an input sample beam;
means for producing an output sample beam comprising a retinal image from an eye;
means for adjusting the focus of said input sample beam into said eye, wherein said eye will reflect a portion of said input sample beam to produce an output sample beam;
a reference beam path configured to produce an output reference beam that has traveled the same distance as said input sample beam combined with said output sample beam; and
means for combining said output reference beam and said output sample beam to produce a combined output beam, wherein said combined output beam comprises an interference pattern produced from the combination of said output reference beam with said output sample beam.

2. The apparatus of claim 1, wherein said means for adjusting comprises a Badal optometer configured for adjusting the focus of said input sample beam into said eye.

3. A method, comprising
providing an input beam;
splitting said input beam into a reference beam and an input sample beam;
producing an output sample beam comprising a retinal image from an eye;
adjusting the focus of said input sample beam into said eye, wherein said eye will reflect a portion of said input sample beam to produce an output sample beam; and
producing an output reference beam that has traveled the same distance as said input sample beam combined with said output sample beam; and
combining said output reference beam and said output sample beam to produce a combined output beam, wherein said combined output beam comprises an interference pattern produced from the combination of said output reference beam with said output sample beam.

4. The method of claim 3, wherein the step of adjusting uses a Badal optometer configured for adjusting the focus of said input sample beam into said eye.

* * * * *